United States Patent
Pratt

(10) Patent No.: US 7,255,380 B1
(45) Date of Patent: Aug. 14, 2007

(54) BOTTOM-EMPTYING DEVICE FOR TAPERED BAILER

(76) Inventor: David W. Pratt, 13512 Feather Sound Cir., Apt. 1401, Clearwater, FL (US) 33762

( * ) Notice: Subject to any disclaimer, the term of this patent is extended or adjusted under 35 U.S.C. 154(b) by 350 days.

(21) Appl. No.: 10/707,291

(22) Filed: Dec. 3, 2003

(51) Int. Cl.
*G01N 1/12* (2006.01)

(52) U.S. Cl. ................. 294/68.25; 73/864.63
(58) Field of Classification Search ............ 294/68.25; 73/864.63; 166/162, 167, 168, 264, 267
See application file for complete search history.

(56) References Cited

U.S. PATENT DOCUMENTS

| | | | | |
|---|---|---|---|---|
| 3,295,686 A | * | 1/1967 | Krueger | 210/455 |
| 4,590,810 A | * | 5/1986 | Hunkin et al. | 73/864.63 |
| 5,139,654 A | * | 8/1992 | Carpenter | 73/864.83 |
| 5,878,813 A | * | 3/1999 | Ridgeway, Jr. | 73/864.63 |
| 6,695,053 B2 | * | 2/2004 | Stewart | 166/162 |
| 6,913,152 B2 | * | 7/2005 | Zuk, Jr. | 210/406 |
| 6,966,587 B1 | * | 11/2005 | Pratt | 294/68.22 |

* cited by examiner

*Primary Examiner*—Patrick Mackey
*Assistant Examiner*—Paul T Chin
(74) *Attorney, Agent, or Firm*—Ronald E. Smith; Smith & Hopen, P.A.

(57) ABSTRACT

A bailer has a tapered leading end to reduce agitation and turbidity as the bailer is introduced into a body of liquid fluid. A check valve is unseated and admits liquid fluid into the bailer as the bailer enters the liquid fluid. The check valve is seated and seals the liquid fluid within the bailer against leakage when the bailer is retrieved from the liquid fluid. A first embodiment includes a bottom-emptying device that guides liquid fluid in the bailer into a wide-mouth container. A second embodiment includes a bottom-emptying device that guides the liquid fluid into a narrow mouth container such as a vial. In both embodiments, the bottom-emptying device is tapered and engages the outside walls of the tapered leading end of the bailer. This prevents liquid fluid from wetting a user's hands when the bottom-emptying device is used to unseat the check valve.

9 Claims, 5 Drawing Sheets

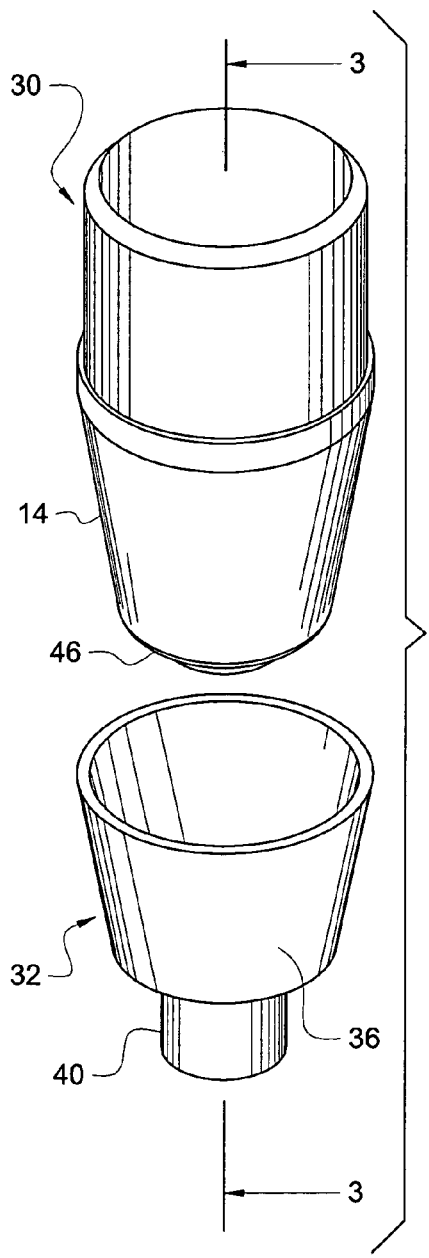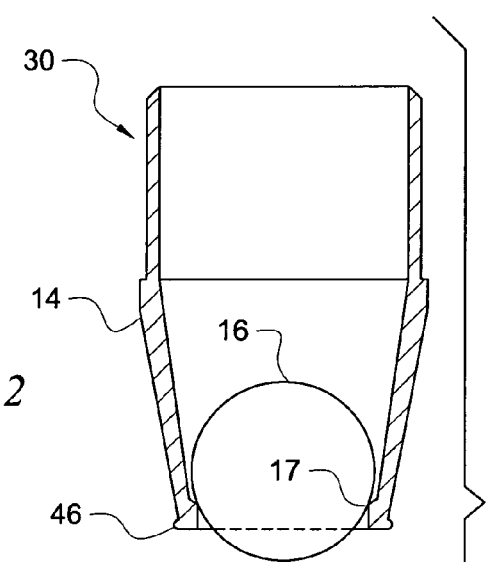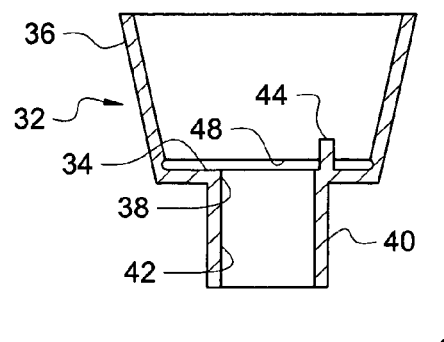
FIG. 2
FIG. 3

BOTTOM-EMPTYING DEVICE FOR TAPERED BAILER

BACKGROUND OF INVENTION

1. Field of the Invention

This invention relates, generally, to bailers. More particularly, it relates to a bottom-emptying device that engages the outside of a bailer.

2. Description of the Prior Art

Common bailers agitate the liquid fluid into which they are dropped, thereby increasing the turbidity of the sample that is collected. Turbid samples are unacceptable for environmental analysis because the particulate matter contained therein is introduced into the sample by the agitation created by the sample collection process. The collected sample thus does not represent the liquid fluid in the body of water.

A co-pending patent application by the present inventor, entitled "Bailer With Tapered And Ogive Nose Cones," application Ser. No. 10/248,378, filed Jan. 15, 2003, substantially solves the agitation and turbidity problem by providing a bailer having a tapered leading end. The taper allows the bailer to slice into the liquid fluid with a minimum of agitation and thus a minimum of turbidity.

A free-floating ball is positioned within the tapered leading end. The tapered leading end is therefore sometimes referred to as a valve housing. When the free-floating ball is fully seated within a valve seat formed on an interior surface of the valve housing, liquid fluid within the hollow interior of the bailer is sealed within said hollow interior. When the free-floating ball is unseated from the valve seat, liquid fluid within the hollow interior of the bailer flows past the unseated ball and into the lumen of a downspout. Thus the ball is understood to serve as a check valve.

The downspout has a wide diameter if the liquid fluid is drained into a wide-mouth container and the downspout has a narrow diameter if the liquid fluid is drained into a vial or a test tube.

Bailers are best emptied from the bottom because unacceptable amounts of oxygen are introduced into the sample if the bailer is decanted from the top.

Various devices have been developed to facilitate bottom-emptying, but the known devices do not perform the emptying process in an optimal manner. For example, a user must insert such devices into the hollow interior of the bailer from the lowermost end of the bailer. The liquid fluid starts to flow from the bailer as soon as the ball that serves as a check valve is unseated. The hands of the person handling the bottom-emptying device are therefore wetted. If the liquid fluid is highly acidic or otherwise dangerous, use of such a bottom-emptying device is unacceptable, Even if the fluid is not dangerous, the user may not care to get his or her hands wet, especially during cold weather.

An improved bottom-emptying device is therefore needed. The improved device would be easy to install but would not result in wetting of a user's hand.

However, in view of the prior art considered as a whole at the time the present invention was made, it was not obvious to those of ordinary skill in the pertinent art how the art could be advanced to provide a bottom-emptying device that prevents a user's hands from coming into contact with the liquid fluid being drained from a bailer.

SUMMARY OF INVENTION

The long-standing but heretofore unfulfilled need for a bailer bottom-emptying device that prevents a user's hands from coming into contact with the liquid within the hollow interior of a bailer during a bottom-emptying procedure is now met by a new, useful, and nonobvious invention.

The novel bottom-emptying device of this invention is used with a bailer having a cylindrical main body and a downwardly tapered leading end or valve housing. The trailing end of the bailer is adapted to be engaged by a means for lowering the bailer into a body of liquid fluid and for raising the bailer from the body of liquid fluid.

The leading end of the bailer is a frusto-conical valve housing that is secured, preferably by welding, to the leading end of the cylindrical main body. The valve housing has a leading end that has a diameter less than its trailing end and the trailing end of the valve housing has a diameter substantially equal to a diameter of the cylindrical main body of the bailer. The valve housing significantly reduces agitation and suppresses turbidity when the bailer is introduced into a body of liquid fluid.

A first embodiment of the novel emptying device is adapted to guide liquid fluid in the bailer into a wide-mouth container. A second embodiment of the novel emptying device is adapted to guide liquid fluid in the bailer into a narrow-mouth container such as a vial or test tube.

In both embodiments, the bottom-emptying device has a trailing end that slidingly receives the tapered leading end or valve housing of the bailer. Thus, the novel bottom-emptying device is releasably secured to the exterior surface of the valve housing. Thus, the user's hands are positioned above the downspout when the liquid fluid begins flowing from the bailer.

An important object of this invention is to provide a bailer bottom-emptying device that does not cause a user's hands to come into contact with liquid fluid during the bailer-emptying process.

A closely related object is to provide a bottom-emptying device suitable for use with bailers having tapered leading ends.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which:

FIG. 2 is an exploded perspective view of a first embodiment of the novel bottom-emptying device when used with a tapered valve housing;

FIG. 3 is a sectional view taken along line 2-2 in FIG. 1;

DETAILED DESCRIPTION

Figure 1:
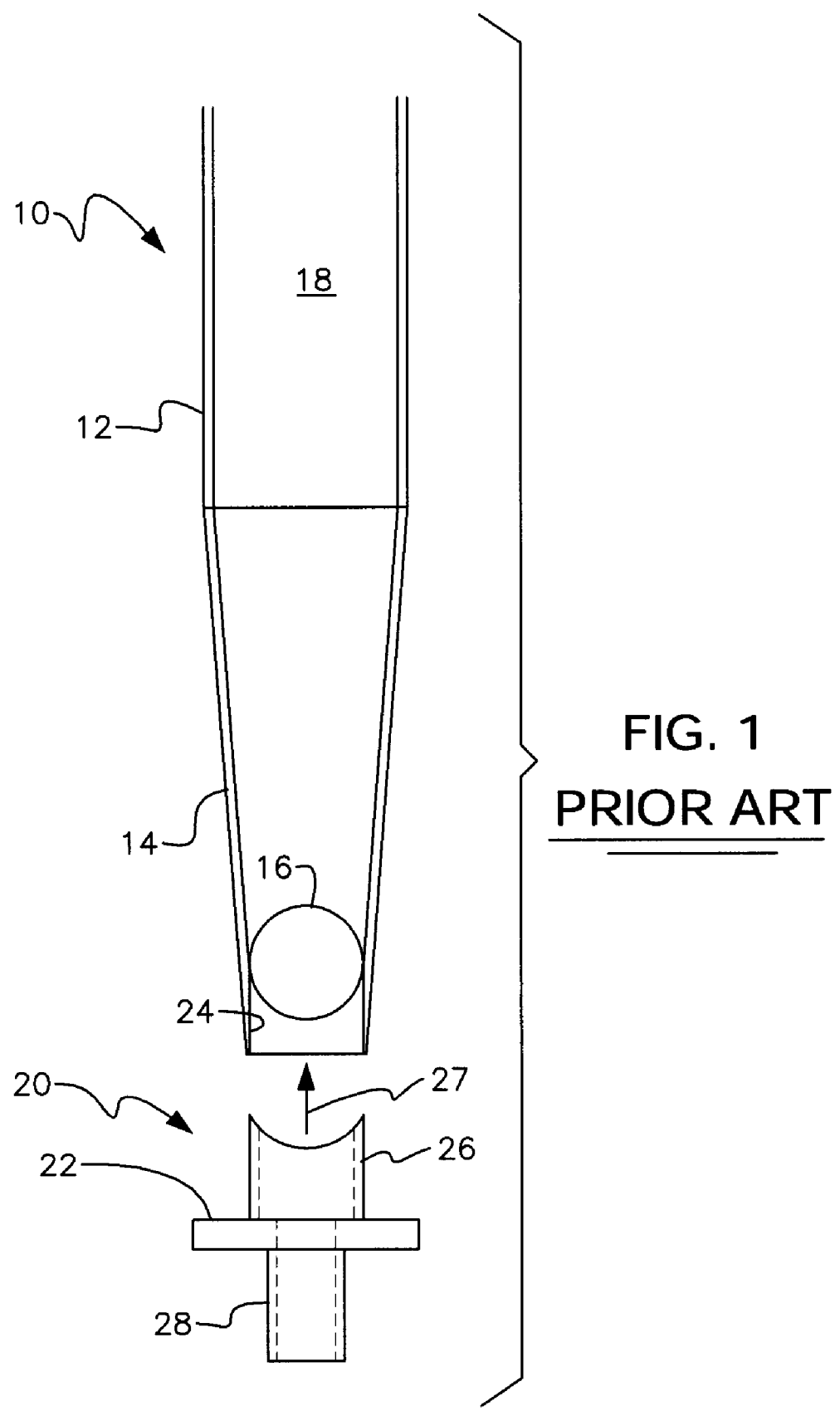
FIG. 1 is an exploded side elevational view of a bottom-emptying device of the prior art when used with a novel bailer having a tapered valve housing.

Referring to the front elevational view of FIG. 1, it will there be seen that the reference numeral 10 denotes a prior art bailer having a cylindrical main body 12 and a leading end having tapered sidewalls 14. Free-floating ball 16 is a check valve. It is unseated to admit liquid fluid into the hollow interior 18 of bailer 10 when the bailer enters into liquid fluid and it is seated to prevent leakage of liquid fluid from said hollow interior when the bailer is retrieved from the liquid fluid.

Other types of check valves are also within the scope of this invention. For example, see the check valve in U.S. Pat. No. 6,457,486 entitled "Bailer Having Leak-Inhibiting Seal" to the present inventor.

Prior art bottom-emptying device 20 includes flange 22 that has a diameter greater than that of opening 24 of said leading end 14 to limit the depth of insertion of ball-unseating member 26. Said ball-unseating member 26 has a tubular construction and an outer diameter less than the diameter of opening 24 so that said unseating member 26 may slideably enter into opening 24, as indicated by directional arrow 27, and unseat ball valve 16.

Downspout 28 also has a tubular construction and guides liquid fluid flowing out of hollow interior 18 into a wide-mouth container.

It should be observed that a user must grasp flange 22 or downspout 28 to insert bottom-emptying device 20 into tapered leading end 14 because, as aforesaid, upper part 26 thereof must enter into the hollow interior of said tapered leading end. The liquid fluid begins flowing out of the bailer as soon as ball 16 is unseated and the user's hand is therefore contacted by said liquid fluid.

The first embodiment of the present invention is depicted in FIGS. 2-5 and is denoted 30 as a whole. The parts thereof in common with the prior art bailer of FIG. 1 are denoted by the same reference numerals. The annular seat for ball valve 16 is denoted 17 in FIG. 2.

As depicted in FIG. 3, bailer-emptying device 32 includes flat bottom wall 34 having tapered sidewalls 36 mounted about the periphery thereof. The taper of sidewalls 36 matches the taper of sidewalls 14.

Aperture 38 is formed in bottom wall 34, preferably centrally thereof.

Downspout 40 depends from bottom wall 34. Lumen 42 of downspout 40 is in open fluid communication with aperture 38.

Truncate peg 44 is formed integrally with bottom wall 34 and protrudes upwardly therefrom in upstanding relation thereto.

As depicted in FIG. 2, annular bead 46 is formed in the leading end of tapered walls 14 and as depicted in FIG. 3 a corresponding annular groove 48 is formed in the interior surface of tapered walls 36 of bottom-emptying device 32.

Figure 4:
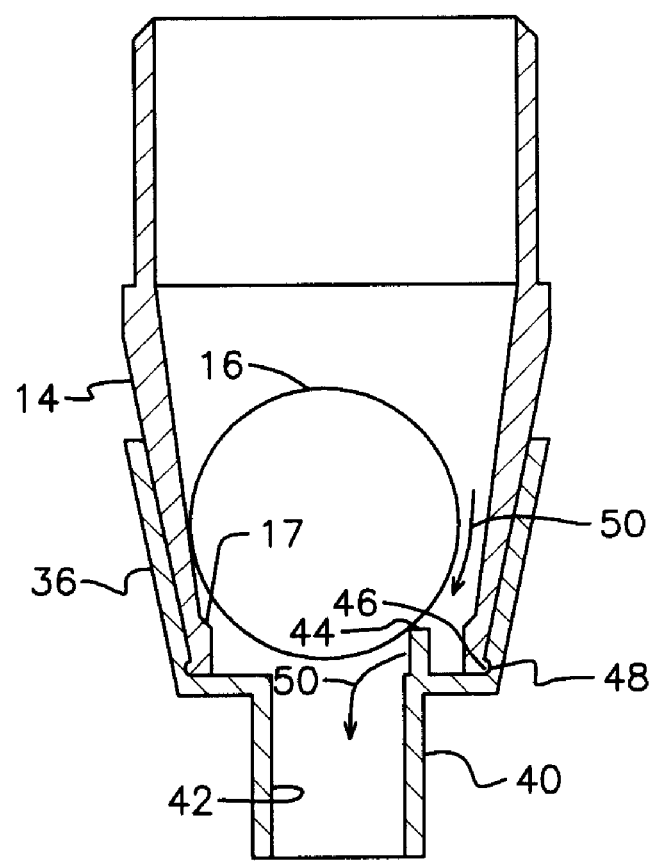
FIG. 4 is a sectional view depicting the unseating of a free-floating check valve.
Figure 5:
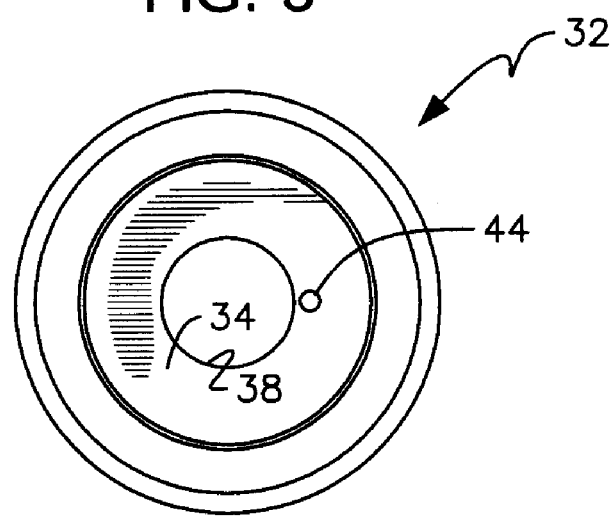
FIG. 5 is a top plan view of the first embodiment of the bottom-emptying device.
Figures 6, 7:
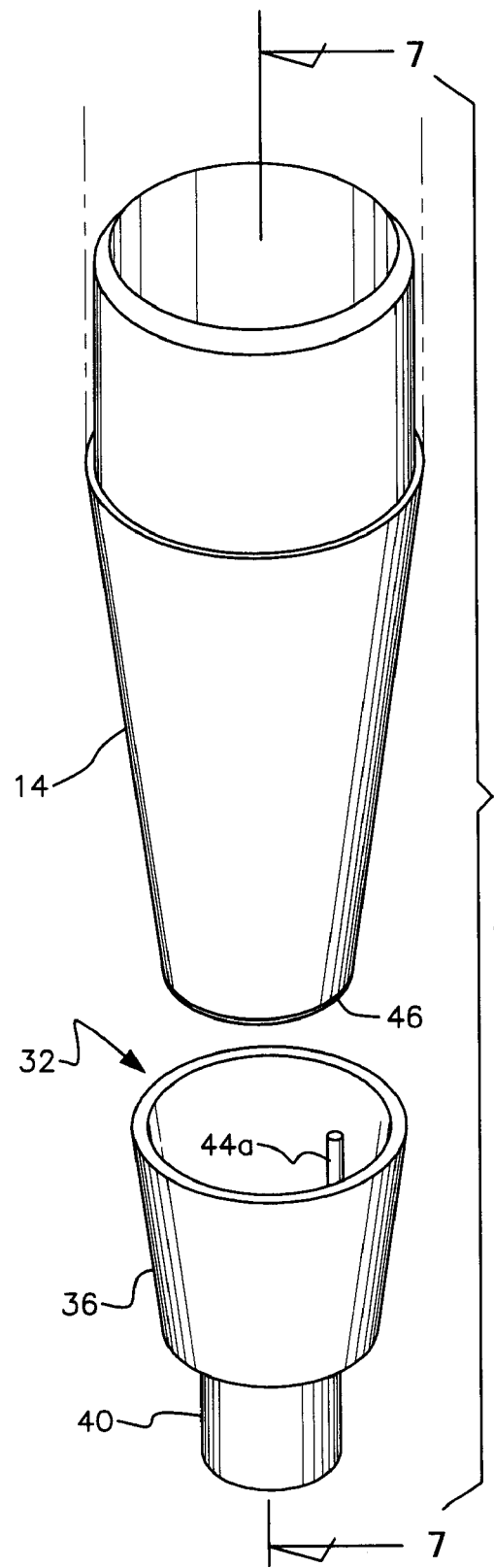
FIG. 6 is a perspective view of a second embodiment.
FIG. 7 is a sectional view taken along line 7-7 in FIG. 6.

The interlocking of said annular bead 46 and annular groove 48 is depicted in FIG. 4. Sidewalls 36 overlie tapered walls 14 and ball valve 16 is unseated from annular seat 17 by truncate peg 44. Liquid fluid flowing out of the bailer is denoted by curvilinear directional arrows collectively denoted 50.

The leading edge of tapered walls 14 is fully seated against bottom wall 34 of bottom-emptying device 32 when bead 46 and groove 48 interlock with one another. Such interlocking allows the user to release bottom-emptying device 32 while waiting for liquid fluid to drain from the bailer. Due to the flexibility and resiliency of the materials from which bottom-emptying device 32 and tapered walls 14 are made, the interlocking of said bead and groove are easily overcome when the draining procedure is completed and bottom-emptying device 32 is detached from tapered sidewalls 14.

Downspout 40 has a relatively large diameter as depicted in FIGS. 2-5 and is best used when guiding liquid fluid into a large-mouth container, not shown.

Figure 8:
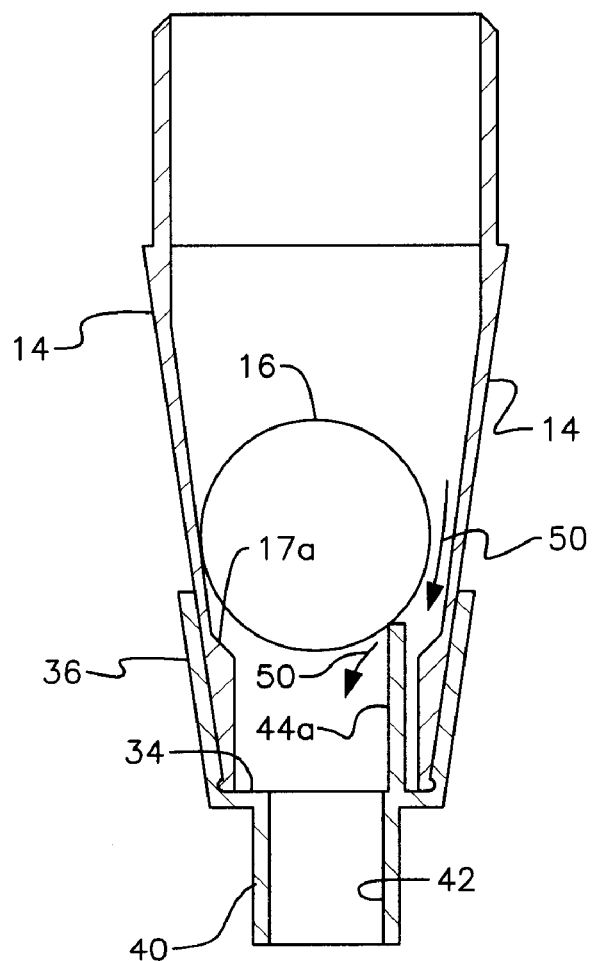
FIG. 8 is a sectional view depicting the unseating of a free-floating check valve by the second embodiment.
Figure 9:
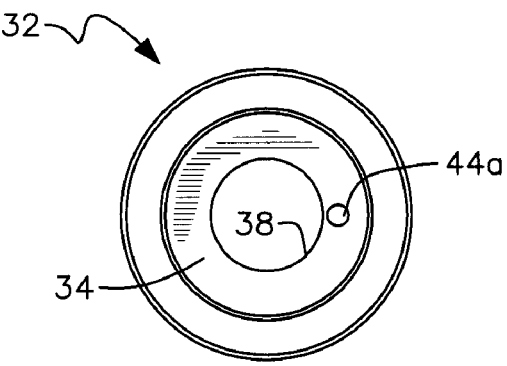
FIG. 9 is a top plan view of the second embodiment of the bottom-emptying device.

A second embodiment is depicted in FIGS. 6-9. This embodiment differs from the first embodiment in that elongate peg 44a supplants truncate peg 44 of the first embodiment because valve seat 17a of this second embodiment positions ball valve 16 in recessed, trailing relation to the open leading end of tapered walls or valve housing 14. The unseating of ball valve 16 from valve seat 17a by elongate peg 44a is depicted in FIG. 8.

In all other respects, as indicated by the common reference numerals, the embodiment of FIGS. 6-9 is like that of the embodiment of FIGS. 2-5.

Figure 10:
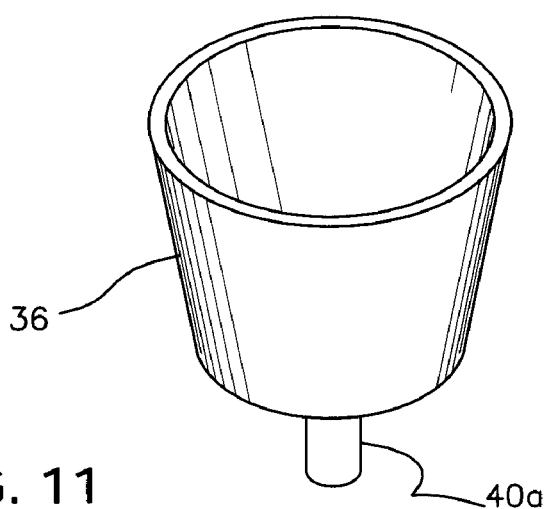
FIG. 10 is a perspective view of a third embodiment of the bottom-emptying device.

A third embodiment is depicted in FIG. 10. It is like the first embodiment (FIGS. 2-5) in all respects, including truncate peg 44, with the exception that downspout 40a has a small diameter. Accordingly, this embodiment of bottom-emptying device 32 is used when a vial or test tube is filled with liquid fluid from a bailer of the type having ball valve 16 positioned at the leading edge thereof as in the structure depicted in said FIGS. 2-5.

Figure 11:
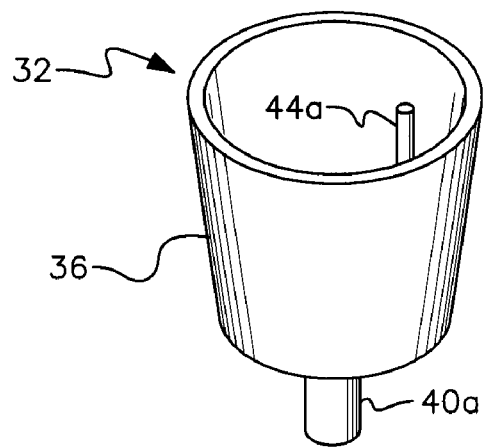
FIG. 11 is a perspective view of a fourth embodiment of the bottom-emptying device.

A fourth embodiment is depicted in FIG. 11. It is like the second embodiment (FIGS. 6-9) in all respects, including elongate peg 44a, with the exception that downspout 40a has a small diameter. Accordingly, this embodiment of bottom-emptying device 32 is used when a vial or test tube is filled with liquid fluid from a bailer having a recessed ball valve 16 as in the structure depicted in FIGS. 6-9.

All embodiments of the novel bottom-emptying device are grasped at tapered walls 36 when attached. The user's hand is thus positioned above downspout 40 or 40a and the liquid fluid being drained from the bailer does not contact the user's hand. The snap-on feature further facilitates the emptying procedure.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

The invention claimed is:

1. A bailer, comprising:

a cylindrical main body;

a valve housing with tapered sidewalls secured to a leading end of said cylindrical main body;

said cylindrical main body having a trailing end adapted to be engaged by a means for lowering said bailer into a body of liquid fluid and for raising said bailer from said body of liquid fluid;

an annular bead formed in a leading end of said tapered sidewalls of said valve housing, said annular bead being formed in an external surface of said valve housing tapered sidewalls;

a check valve disposed in said valve housing;

a bottom-emptying device having a bottom wall and tapered sidewalls mounted about a periphery of said bottom wall;

said bottom-emptying device adapted to fully receive said valve housing;

said leading end of said valve housing tapered sidewalls disposed in abutting relation to said bottom wall when said valve housing is fully received within said bottom-emptying device;

said tapered sidewalls of said bottom-emptying device overlying the tapered sidewalls of said valve housing when said valve housing is fully received within said bottom-emptying device;

an annular groove formed in an interior surface of said tapered sidewalls of said bottom-emptying device, said annular groove being contiguous to said bottom wall so that said annular bead fits within said annular groove when said valve housing is fully received within said bottom-emptying device, said annular groove removably interlocking with said annular bead and securing said bottom-emptying device to said valve housing;

an aperture formed in said bottom wall;

a downspout depending from said bottom wall, said downspout having a lumen in fluid communication with said aperture;

a peg mounted in upstanding relation to said bottom wall, said peg being positioned adjacent said aperture;

whereby said peg unseats said check valve when said bottom-emptying device is removably secured to said valve housing so that liquid fluid within said bailer flows through said downspout.

2. The bailer of claim 1, further comprising:

said peg having a truncate extent and having utility with said bailer having a check valve positioned at a leading end of said valve housing.

3. The bailer of claim 2, further comprising:

said downspout having a predetermined diameter adapted to guide liquid into a wide-mouth container.

4. The bailer of claim 2, further comprising:

said downspout having a predetermined diameter adapted to guide liquid into a vial.

5. The bailer of claim 1, further comprising:

said peg having an elongate extent and having utility with said bailer having a check valve positioned in recessed relation to a leading end of said valve housing.

6. The bailer of claim 3, further comprising:

said downspout having a predetermined diameter adapted to guide liquid into a wide-mouth container.

7. The bailer of claim 3, further comprising:

said downspout having a predetermined diameter adapted to guide liquid into a vial.

8. The bailer of claim 1, further comprising:

said downspout having a predetermined diameter adapted to guide liquid into a wide-mouth container.

9. The bailer of claim 1, further comprising:

said downspout having a predetermined diameter adapted to guide liquid into a vial.

* * * * *